United States Patent
Stockdale et al.

(10) Patent No.: US 10,751,141 B2
(45) Date of Patent: Aug. 25, 2020

(54) MEDICAL DEVICE TRAY TRACKING SYSTEM AND METHOD OF USE

(71) Applicants: Matt Stockdale, Des Moines, IA (US); Mike Higgins, Des Moines, IA (US)

(72) Inventors: Matt Stockdale, Des Moines, IA (US); Mike Higgins, Des Moines, IA (US)

(73) Assignee: STOCKDALE MEDICAL, LLC, West Des Moines, IA (US)

( * ) Notice: Subject to any disclaimer, the term of this patent is extended or adjusted under 35 U.S.C. 154(b) by 0 days.

(21) Appl. No.: 16/241,203

(22) Filed: Jan. 7, 2019

(65) Prior Publication Data

US 2019/0209258 A1 Jul. 11, 2019

Related U.S. Application Data

(60) Provisional application No. 62/614,530, filed on Jan. 8, 2018.

(51) Int. Cl.
| | | |
|---|---|---|
| *A61B 50/33* | (2016.01) | |
| *A61B 50/20* | (2016.01) | |
| *G16H 40/20* | (2018.01) | |
| *A61B 90/98* | (2016.01) | |
| *A61B 90/92* | (2016.01) | |
| *G16H 40/67* | (2018.01) | |
| *G06Q 10/08* | (2012.01) | |
| *A61B 50/30* | (2016.01) | |

(52) U.S. Cl.
CPC .............. *A61B 50/33* (2016.02); *A61B 50/20* (2016.02); *A61B 90/92* (2016.02); *A61B 90/98* (2016.02); *G16H 40/20* (2018.01); *G16H 40/67* (2018.01); *A61B 2050/3011* (2016.02); *G06Q 10/087* (2013.01)

(58) Field of Classification Search
None
See application file for complete search history.

(56) References Cited

U.S. PATENT DOCUMENTS

| | | | |
|---|---|---|---|
| 2011/0227722 A1* | 9/2011 | Salvat, Jr. ............. | G01S 5/0027 340/539.1 |
| 2014/0085084 A1* | 3/2014 | Ghazarian ............ | H04W 4/023 340/539.13 |
| 2014/0288952 A1* | 9/2014 | Smith .................. | G06Q 10/087 705/2 |
| 2015/0068942 A1* | 3/2015 | Gerstner ............... | A61B 50/30 206/370 |

(Continued)

*Primary Examiner* — Thomas S McCormack
(74) *Attorney, Agent, or Firm* — Christopher A. Proskey; BrownWinick Law Firm (57) ABSTRACT

A medical device tray tracking system is presented that includes a medical device tray having a plurality of medical devices thereon that are configured to be used in the performance of a medical procedure. The system also includes a tracking device that is configured to be attached to the medical device tray, the tracking device having a housing, a controller having a microprocessor and memory, a communications module having a transceiver and an antenna that facilitates wireless communication, and a power source that powers electronic components of the tracking device. The system also includes a third party intermediary that provides a user interface and a database that facilitates the transmission of status updates regarding the location of the tracking device and associated medical device tray.

34 Claims, 3 Drawing Sheets

(56) References Cited

U.S. PATENT DOCUMENTS

2015/0356497 A1* 12/2015 Reeder ................. G06Q 10/087
                                                        705/28
2017/0181645 A1*  6/2017 Mahalingam ........ A61B 5/0004
2019/0187819 A1*  6/2019 Ullrich .................... G06F 3/016

* cited by examiner

MEDICAL DEVICE TRAY TRACKING SYSTEM AND METHOD OF USE

CROSS REFERENCE TO RELATED APPLICATIONS

This patent application claims priority to provisional patent application Ser. No. 62/614,530 filed on Jan. 8, 2018 entitled "Medical Device Tray Tracking System and Method of Use," which is fully incorporated by reference herein.

FIELD OF THE DISCLOSURE

This disclosure relates to delivery of medical devices. More specifically, and without limitation, this disclosure relates to a system and method of tracking medical device trays.

BACKGROUND OF THE DISCLOSURE

With advances in medicine the complexity and sophistication of medical procedures has increased exponentially. As a result, many of these advanced medical procedures require an array of highly specialized medical devices to perform the procedure. These medical devices, which can include medical tools, medical implants, medical devices, medical equipment and medical consumables, among other devices, are often consolidated and laid out in a convenient manner for the surgeon and other medical staff on what are known as medical trays, or simply trays. These trays are specifically built and assembled for specific procedures. Due to the highly specialized contents of the trays, assembled trays can be valued in the tens to hundreds of thousands of dollars. Due to the highly specialized contents of these trays, it can take in excess of six-months to build and/or rebuild a tray with the needed contents.

In practice, these trays are shipped around the country and around the world when and where they are needed. This shipping occurs through a network of sales representatives, or simply sales reps and shipping agents, such as common carriers and specialized carriers, among others.

Despite the extremely high value of these trays, these trays are shipped without any ability to track the present whereabouts of the trays. Due to the present inability to track these trays, this often results in missing, lost and/or misplaced trays.

Lost or misplaced trays can have disastrous effects. A lost or misplaced tray can cause the delay or inability to perform a needed medical procedure when and where needed. A lost or misplaced tray may require another tray to be built, which has huge financial impacts. A lost or misplaced tray can cause a delay in payment to hospitals, surgeons, sales reps and others involved in the process. A lost tray can cause substantial insurance claims.

Another problem with the inability to track these highly valuable trays is that it causes unnecessary risk to the parties involved. As an example, sales reps involved in the distribution process are responsible for the care and custody of the trays once they take possession. As such, the sales rep is held responsible when the trays go lost or missing. The sales rep may be held liable even if they had nothing to do with the tray being lost or going missing. This can cause insurance claims, loss of income and a higher cost of doing business.

For all of these reasons stated above, and the reasons stated below, there is a need in the art for an improved medical device tray tracking system and method of use.

Thus, it is a primary object of the disclosure to provide a medical device tray tracking system and method of use that improves upon the state of the art.

Another object of the disclosure is to provide a medical device tray tracking system and method of use that provides the ability to track the location of medical trays.

Yet, another object of the disclosure is to provide a medical device tray tracking system and method of use that improves the ability to track the location of medical trays.

Another object of the disclosure is to provide a medical device tray tracking system and method of use that reduces the number of lost or misplaced medical trays.

Yet, another object of the disclosure is to provide a medical device tray tracking system and method of use that reduces the cost of medical procedures.

Another object of the disclosure is to provide a medical device tray tracking system and method of use that improves the efficiency of medical procedures.

Yet, another object of the disclosure is to provide a medical device tray tracking system and method of use that reduces the risk to medical sales reps for lost or misplaced medical trays.

Another object of the disclosure is to provide a medical device tray tracking system and method of use that reduces insurance claims due to lost or misplaced medical trays.

Yet, another object of the disclosure is to provide a medical device tray tracking system and method of use that reduces the need to build or rebuild existing medical trays.

Another object of the disclosure is to provide a medical device tray tracking system and method of use that improves the efficiency of our medical system.

Yet, another object of the disclosure is to provide a medical device tray tracking system and method of use that reduces the potential for delay in medical procedures due to a lost or misplaced medical tray.

Another object of the disclosure is to provide a medical device tray tracking system and method of use that lowers the cost of healthcare.

Yet, another object of the disclosure is to provide a medical device tray tracking system and method of use that is easy to use.

Another object of the disclosure is to provide a medical device tray tracking system and method of use that is safe to use.

Yet, another object of the disclosure is to provide a medical device tray tracking system and method of use that is easy to implement.

Another object of the disclosure is to provide a medical device tray tracking system and method of use that is practically foolproof.

Yet, another object of the disclosure is to provide a medical device tray tracking system and method of use that does not substantially increase the cost of delivery.

Another object of the disclosure is to provide a medical device tray tracking system and method of use that has a robust design.

Yet, another object of the disclosure is to provide a medical device tray tracking system and method of use that has a long useful life.

Another object of the disclosure is to provide a medical device tray tracking system and method of use that is durable.

Yet, another object of the disclosure is to provide a medical device tray tracking system and method of use that is relatively inexpensive.

Another object of the disclosure is to provide a medical device tray tracking system and method of use that is high quality.

These and other objects, features, or advantages of the disclosure will become apparent from the specification, figures and claims.

SUMMARY OF THE DISCLOSURE

A medical device tray tracking system and method of use is presented that includes a medical device tray having a plurality of medical devices thereon that are configured to be used in the performance of a medical procedure. The system also includes a tracking device that is configured to be attached to the medical device tray, the tracking device having a housing, a controller having a microprocessor and memory, a communications module having a transceiver and an antenna that facilitates wireless communication, and a power source that powers electronic components of the tracking device. The system also includes a third party intermediary that provides a user interface and a database that facilitates the transmission of status updates regarding the location of the tracking device and associated medical device tray. In use, when the tracking device is attached to the medical device tray, the tracking device communicates through a wireless network over the internet and provides information regarding the tracking device and attached medical device tray to the third party intermediary. The system also allows a user to connect to the third party intermediary to determine the most recent status of the tracking device. This system provides up to date status and location of medical device trays, helps to prevent lost or misplaced medical device trays, and saves time, money and potentially lives.

DETAILED DESCRIPTION OF THE DISCLOSURE

In the following detailed description, reference is made to the accompanying drawings which form a part hereof, and in which is shown by way of illustration specific embodiments in which the disclosure may be practiced. These embodiments are described in sufficient detail to enable those skilled in the art to practice the disclosure, and it is to be understood that other embodiments may be utilized and that mechanical, procedural, and other changes may be made without departing from the spirit and scope of the disclosure(s). The following detailed description is, therefore, not to be taken in a limiting sense, and the scope of the disclosure(s) is defined only by the appended claims, along with the full scope of equivalents to which such claims are entitled.

As used herein, the terminology such as vertical, horizontal, top, bottom, front, back, end, sides, left, right, and the like are referenced according to the views, pieces, parts, components and figures presented. It should be understood, however, that the terms are used only for purposes of description, and are not intended to be used as limitations. Accordingly, orientation of an object or a combination of objects may change without departing from the scope of the disclosure.

Figure 1:
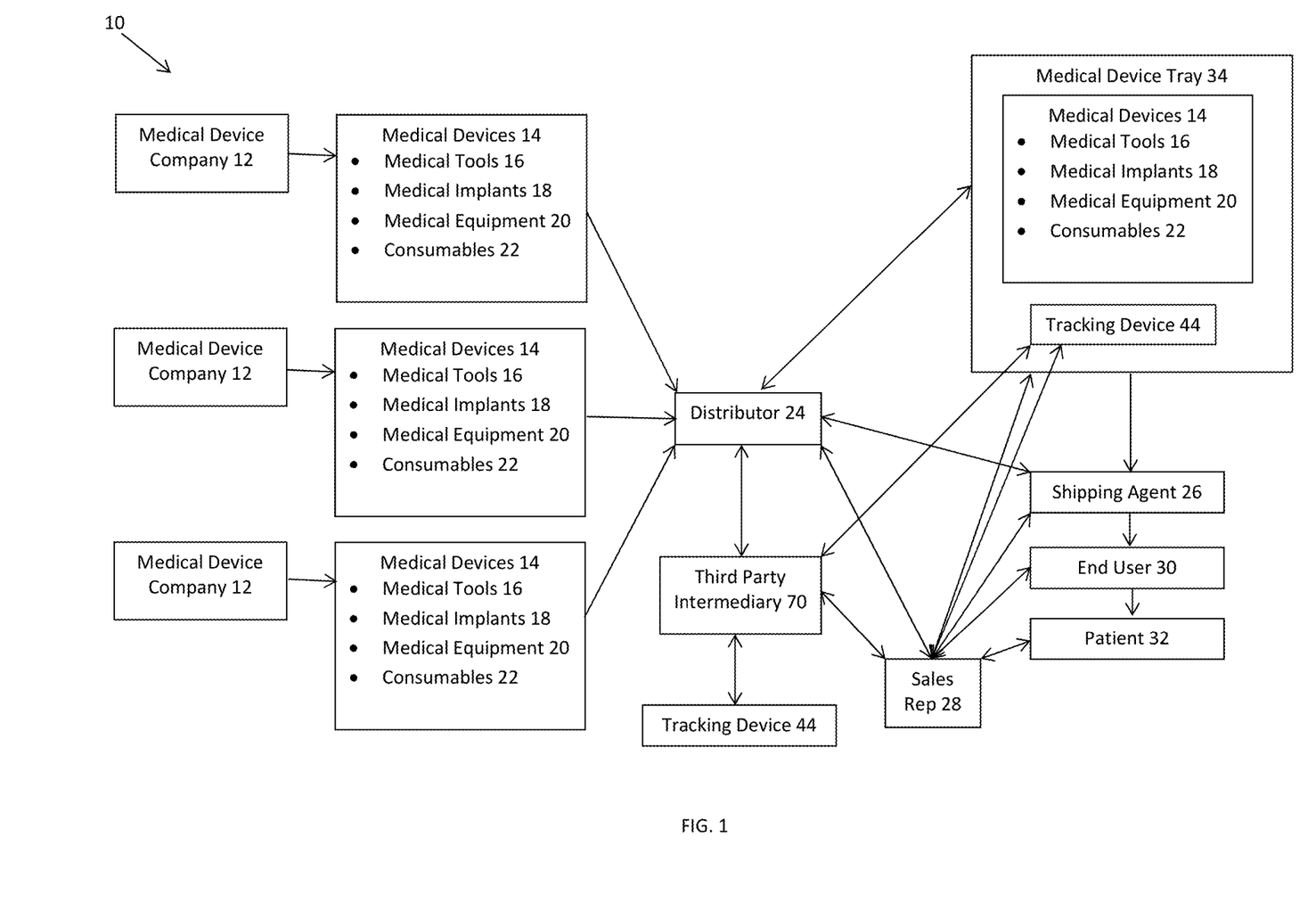
FIG. 1 is a plan view of a medical device tray tracking system and method of use described herein.
Figure 2:
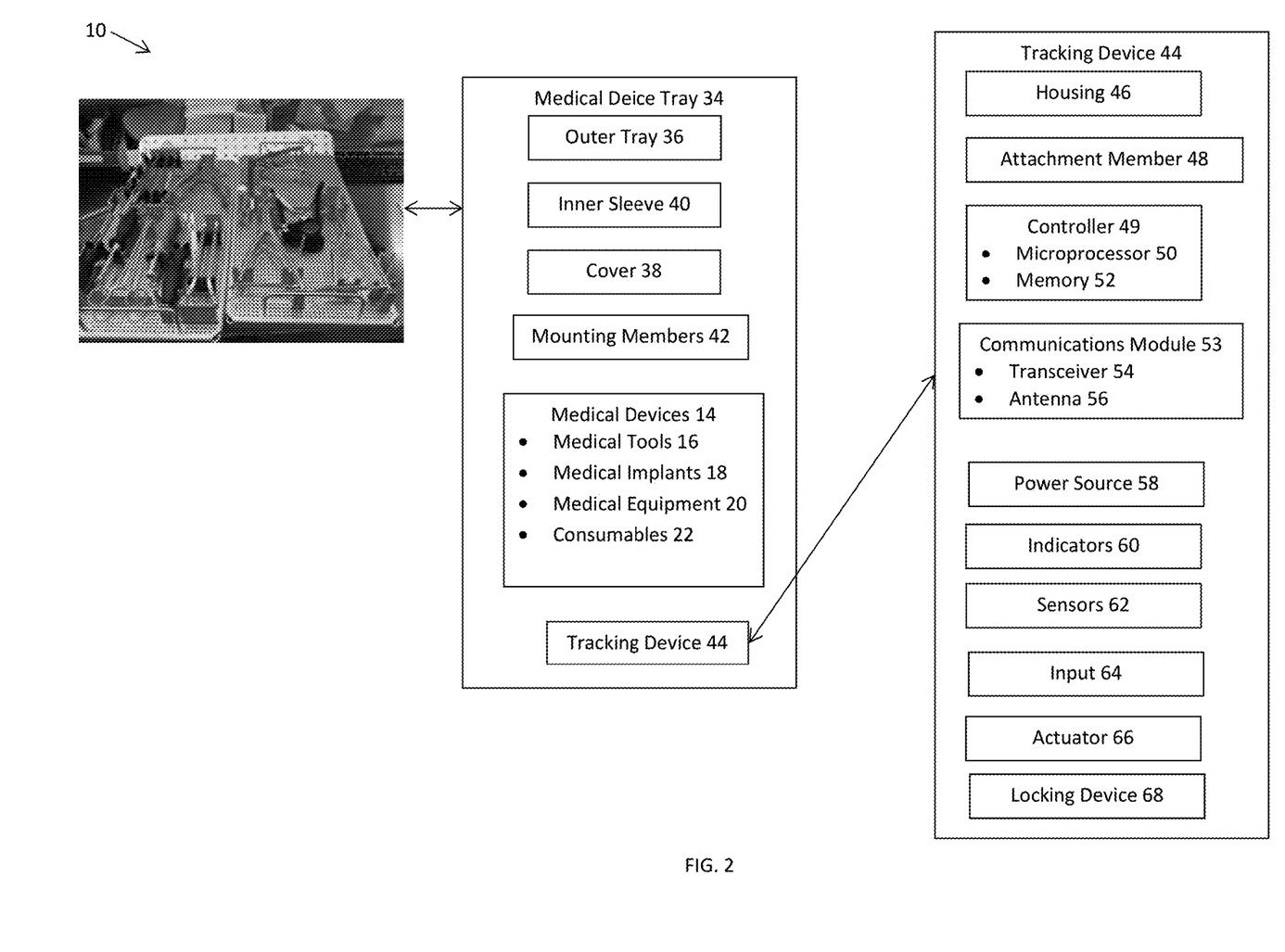
FIG. 2 is another plan view of a medical device tray tracking system and method of use described herein, the view showing additional features of the tray and the tracking device.
Figure 3:
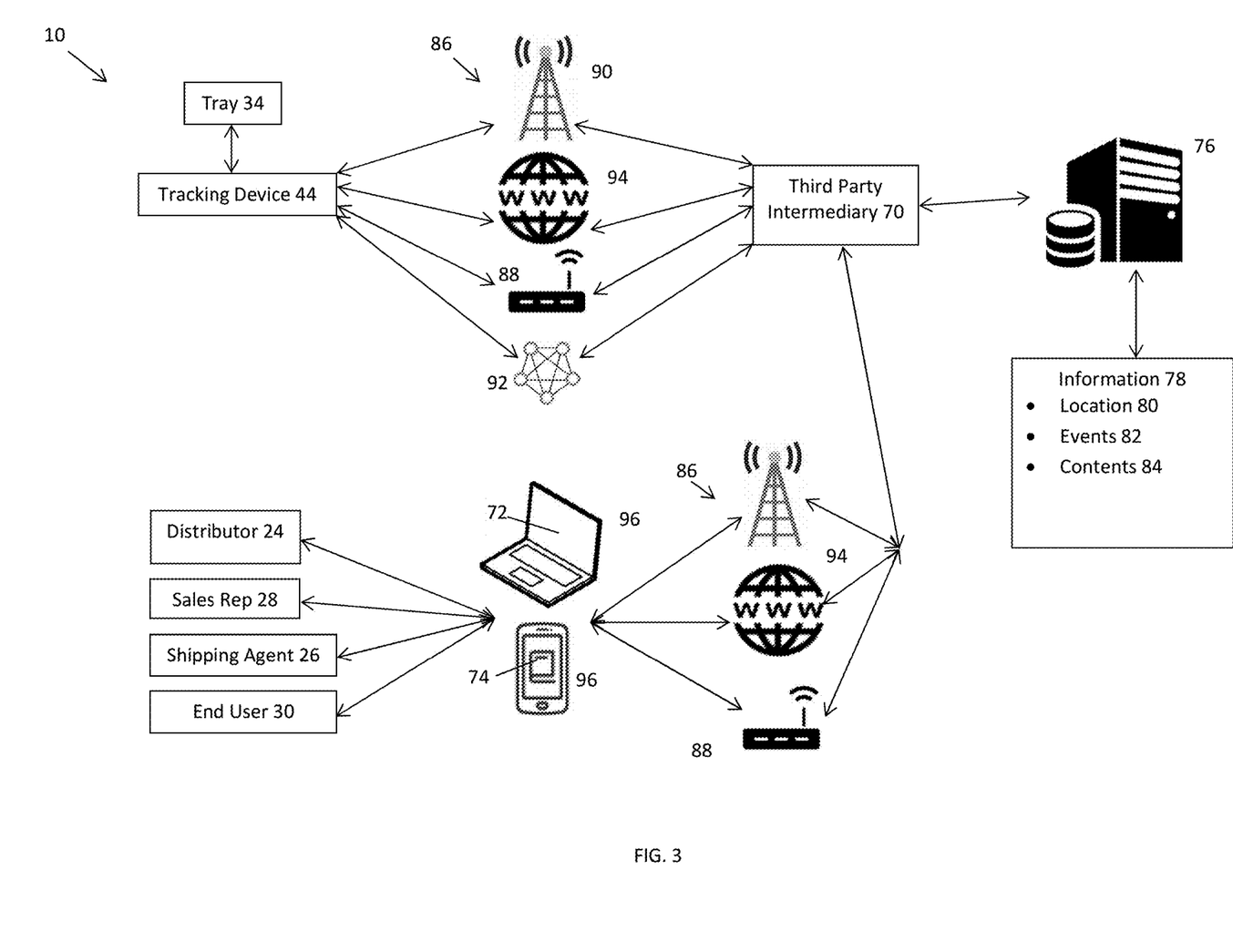
FIG. 3 is another plan view of a medical device tray tracking system and method of use described herein, the view showing additional features of the user interface and information distribution.

With reference to the figures, a medical device tray tracking system 10, or simply system 10, is presented. As one example, the medical device tray tracking system 10 includes: one or more medical device companies 12 that manufacture medical devices 14 including medical tools 16, medical implants 18, medical equipment 20, and medical consumables 22, among others; one or more distributors 24; one or more shipping agents 26; one or more sales representatives 28; one or more end users 30; one or more patients 32; one or more trays 34 that include an outer tray 36, a cover 38, an inner sleeve 40, and mounting members 42; one or more tracking devices 44 having a housing 46, an attachment member 48, a controller 49 having a microprocessor 50 and memory 52, a communications module 53 having a transceiver 54, and an antenna 56, a power source 58, indicators 60, sensors 62, an input 64, an actuator 66, and a locking device 68; a third party intermediary 70 having a user interface 72, an application 74, a database 76 that includes information 78 including location 80, events 82 and content 84; a wireless network 86 which may include a local network 88, a cellular network 90, a mesh network 92, and the internet 94; a computing device 96 among other components as is shown and described herein.

Medical Device Company:

Medical device company 12 is any entity that manufactures, builds, distributes, handles, imports, sells or is otherwise involved with medical devices 14 that are used in association with medical device tray 34. The system 10 may involve one or any number of medical device companies 12.

Medical Devices:

Medical devices 14 are formed of any suitable size, shape and design and is configured to facilitate a medical purpose. Medical devices 14 are often highly specialized and are configured for a particular purpose. As such, for many medical procedures many highly specialized medical device 14 are needed. The term medical device 14 as used herein is intended to be construed as any device used in association with a medical procedure. In one arrangement, medical devices 14 can be broken down into the following categories: medical tools 16, medical implants 18, medical equipment 20 and medical consumables 22, among any other category.

Medical Tools:

In one arrangement, as one example, medical devices 14 may include a medical tool 16. Medical tools 16 are formed of any suitable size, shape and design and are configured to be used in the performance of a medical procedure. In one arrangement, medical tools 16 may include a scalpel, a clamp, a hammer, a chisel, a tongs, a scissors, a drill, or any other tool used in association with a medical procedure.

Medical Implant:

In one arrangement, as one example, medical devices 14 may include a medical implant 18. Medical implants 18 are formed of any suitable size, shape and design and are configured to be used in the performance of a medical procedure and in some arrangements may be configured to be placed within the body of the patient 32 where it facilitates a medical purpose. In one arrangement, medical implants 18 may include screws, bolts, connectors, clamps, stents, joints, pace makers, artificial valves, or any other form of an implant used in association with a medical procedure.

Medical Equipment:

In one arrangement, as one example, medical devices 14 may include medical equipment 20. Medical equipment 20 may be formed of any suitable size, shape and design and are configured to be used in the performance of a medical procedure. In one arrangement, medical equipment 20 includes specialized equipment that is used in association with medical tools 16 and/or medical implants 18 to help facilitate the use of medical tools 16 and/or medical implants 18 and/or the performance of the medical procedure and may include catheters, diagnostic equipment, scopes, stabilizers; guides, or any other form of medical equipment 20 used in association with a medical procedure.

Medical Consumables:

In one arrangement, as one example, medical devices 14 may include medical consumables 22. Medical consumables 22 may be formed of any suitable size, shape and design and are configured to be used in the performance of a medical procedure. In one arrangement, medical consumables 22 includes specialized equipment that is used in association with medical tools 16 and/or medical implants 18 during the performance of a medical procedure and are consumed or used and discarded after use and may include catheters, placement devices, sponges, tubes, clamps or any other consumable device used in association with a medical procedure.

Distributor:

Due to the specialized nature of the medical procedures that medical device tray 34 is intended to facilitate, medical device tray 34 often includes highly specialized medical devices 14 that are sourced from several different medical device companies 12. In this arrangement, distributor 24 is any entity that sources the medical devices 14 needed to populate and complete medical device tray 34 from one or more medical device companies 12 and/or their vendors and assemble the medical device tray 34 therefrom. Distributor 24 may then hold the medical device tray 34 in inventory until it is needed. One or more distributors 24 may use the system 10. In many cases, when medical device tray 34 is needed, distributor 24 places medical device tray 34 into the care and custody of a shipping agent 26 to deliver the medical device tray 34 to the end user 30 and patient 32.

Shipping Agent and Delivery Service:

When medical device tray 34 is needed, due to the highly specialized nature of the medical procedures that medical device tray 34 is intended to facilitate, medical device tray 34 is often not in the geographic location where it is needed. As such, when the need arises for the medical device tray 34, shipping of the medical device tray 34 is often required. Shipping agent 26 is any entity or group of entities that facilitate delivery of medical device tray 34 to the end user 30 and patient 32. Shipping agent 26 may be a common carrier such as FedEx, UPS, USPS, DHL, and the like. Shipping agent 26 may be a highly specialized courier or other delivery entity.

Medical Device Sales Representative:

Due to the fast pace of medical learning and the continuous and fast-paced development of improved medical devices 14, even cutting edge physicians and surgeons (end user 30) are not able to keep up with the newest and state of the art medical processes and procedures. This complexity is coupled with the sophisticated and complex nature of many of the medical procedures that medical device tray 34 is intended to facilitate. Added to this is the relative rarity of many of the medical conditions that are intended to be treated by the medical device tray 34. Medical device sales representative 28, or simply sales rep 28, is any person, group of persons or entity that develops knowledge about the medical devices 14 of medical device tray 34 and the medical procedures medical device tray 34 is intended to perform. Medical device sales representative 28 serves as a liaison between the end user 30 and/or patient 32, on one side, and the medical device company 12 and/or distributor 24 on the other side.

In some arrangements, sales rep 28 provides knowledge and transfers learning to end user 30 and helps the end user 30 select the optimum medical device tray 34 with the optimum medical devices 14. Sales rep 28 serves many important roles including ensuring proper delivery, establishing proper payment, and other tasks associated with the selection, delivery, use and back-end work associated with the sales cycle.

End User and Patient:

The end user 30 of medical device tray 34, in the arrangement presented herein, is any person or entity that selects, orders and/or uses the components of medical device tray 34 which is used for the benefit of patient 32, who is the person or persons or other living animal that has the underlying medical condition that requires the medical procedures that medical device tray 34 is intended to facilitate. In one arrangement, end user is the treating physician, the treating group of doctors, the lead surgeon, the surgery team, the hospital that is performing the medical procedure for patient 32, the hospital that is caring for patient 32, or any other qualified person, group of persons or entity that is providing care for patient 32 and/or making decisions as to what medical procedures to perform on and/or for patient 32.

Patient 32 is the person, persons or animal that has the underlying medical condition that requires the medical procedures that medical device tray 34 is intended to facilitate.

The decisions as to what medical procedures are necessary for patient 32 are often made in association with the care and consultation of a medical device sales representative 28.

Medical Device Tray:

Medical device tray 34 is formed of any suitable size, shape and design and is configured to house and hold a specific array of medical devices 14, such as, for example, medical tools 16, medical implants 18, medical equipment 20 and medical consumables 22, that are needed to perform a medical procedure by an end user 30 on a patient 32. In one arrangement, as one example, the medical device tray 34 is also intended to lay out the portfolio of medical devices 14 in a convenient, fool proof and obvious manner for use during the performance of the medical procedure. Medical device trays 34 may be packaged in a manner that they are sterile or non-sterile. Medical device tray 34 may be formed of a single device or a single tray, or medical device tray 34 may be formed of a plurality of devices or a plurality of trays that are combined together to form a single component or system which is considered the medical device tray 34.

In one arrangement, as one example, as is shown, medical device tray 34 includes an outer tray 36, a cover 38 and one or more inner sleeves 40. Outer tray 36 is formed of any suitable size, shape and design and is configured to provide structural rigidity and protection to the contents of medical device tray 34. In one arrangement, outer tray 36 serves as the frame member and/or bottom and/or surrounding member(s) for medical device tray 34.

Similarly, cover 38 is formed of any suitable size, shape and design and is configured to provide structural rigidity and protection to the contents of medical device tray 34. In one arrangement, cover 38 serves to cover and shield the contents of medical device tray 34 as well as serve to connect with and seal with outer tray 36. In one arrangement, cover 38 is formed in a corresponding size, shape and configuration such that cover 38 and outer tray 36 connect with one another so as to shield and seal the contents of medical device tray 34, therein, during shipping.

In one arrangement, as is shown, medical device tray 34 includes one or more inner sleeves 40. Inner sleeve(s) 40 are formed of any suitable size, shape and design and is configured to fit within medical device tray 34, between outer tray 36 and cover 38, and further serve to receive and hold medical devices 14 thereon. In one arrangement, as one example, as is shown, inner sleeve 40 is formed of a metallic member that establishes a generally flat plane and includes a plurality of mounting members 42 that are connected thereto that clearly identify and securely receive and hold medical devices 14 therein. While inner sleeve 40 may be formed of any material, making inner sleeve 40 out of a metallic material has benefits when using it in a medical operation environment as it can be sterilized. In one arrangement, inner sleeve 40 includes a grid pattern of openings that facilitate connection of mounting members 42 thereto. Also, in one arrangement, inner sleeve 40 includes indicia thereon that helps to identify what medical devices 14 are to be placed at specific parts of the inner sleeve 40. In one arrangement, this indicia is words, markings, outlines of tools or any other indicia that makes it obvious to a user as to what medical devices 14 are to be placed at specific places of the inner sleeve 40.

Mounting members 42 are formed of any suitable size, shape and design and are configured to be attached to the inner sleeve 40 and are configured to securely receive and hold medical devices 14 thereon. In one arrangement, mounting members 42 are configured to connect to inner sleeve 40 by openings in inner sleeve 40 through bolting, screwing, welding, adhering, or by connecting by any other manner, method or means.

In one arrangement, as one example, medical device tray 34 may include a plurality of inner sleeves 40 that can be removed and arranged in various manners for optimal performance during use.

In view of the high cost of medical device trays 34 and the often life-saving importance of medical device trays 34, tracking device 44 is attached to medical device tray 34 to facilitate tracking of the location of medical device tray 34.

Tracking Device:

Tracking device 44 is formed of any suitable size, shape and design and is configured to be attached to medical device tray 34 and to facilitate the tracking of the location of medical device tray 34. In one arrangement, as one example, tracking device 44 includes a housing 46.

Housing 46 is formed of any suitable size, shape and design and is configured to house and protect the other components and parts of tracking device 44. In one arrangement, as one example, housing 46 is a rigid cover member, formed of a metallic and/or plastic or other rigid material that forms a hollow interior that houses the other components of tracking device 44. Housing 46 also includes one or more attachment members 48 that facilitate attachment of housing 46 to medical device tray 24.

Attachment members 48 are formed of any suitable size, shape and design and are configured to facilitate connection of tracking device 44 to medical device tray 34. In one arrangement, as one example, attachment members 48 are openings that are screwed, bolted, zip-tied or otherwise used to connect tracking device 44 to medical device tray 34. In another arrangement, as one example, attachment members 48 are one or more threaded shafts that are configured to be screwed or bolted to medical device tray 34. In another arrangement, attachment members 48 are formed of any other feature or member that facilitates connection to medical device tray 34.

Controller:

Tracking device 44 includes a controller 49. Controller 49 may be formed of any suitable size, shape and design and is configured to control operation of tracking device 44. In one arrangement, controller 49 includes a microprocessor 50, memory 52, and communications module 53 having a transceiver 54 an antenna 56, and is connected to and/or includes a power source 58.

Microprocessor:

Microprocessor 50 is formed of any suitable size, shape and design and is configured to receive information and/or input from the other components of the system 10, processes this input according to instructions stored in memory 52, and in response outputs commands and/or responses. As one example, microprocessor 50 is one or more computer chips or computer processors which may be a multipurpose, clock driven, register based, digital-integrated circuit which accepts binary data as input, processes it according to instructions stored in memory 52, and provides results as output.

Memory:

Memory 52 is formed of any suitable size, shape and is configured to store information, such as software, code and/or data for later retrieval and use by microprocessor 50. As one example, memory 52 is any information storage and retrieval device such as integrated circuits consisting of silicon-based transistors that are used for storage and may be volatile memory or non-volatile memory. Examples of non-volatile memory include flash memory, ROM, PROM, EPROM and EEPROM memory, magnetic memory (such as hard disk drives, floppy disks and magnetic tape drives), FeRAM, CBRAM, PRAM, STT-RAM, SONOS, RRAM, racetrack memory, NRAM, 3D XPoint, and millipede memory, and the like. Examples of volatile memory include dynamic random-access memory (DRAM), and static random-access memory (SRAM), and the like. Any other information storage device may be used as memory 52.

In one arrangement, microprocessor 50 and memory 52 are formed of a single consolidated unit or chip. In another arrangement, microprocessor 50 and/or memory 52 are formed of multiple components that are electrically connected together, which may be geographically located near one another (such as being mounted on the same printed circuit board) or may be located spatially away from one another.

Communications Module:

In one arrangement, controller 49 includes a communications module 53. Communications module 53 is formed of any suitable size, shape and design and is configured to facilitate communication from and/or to tracking device 44. Communications module 53 facilitates communication through any wireless bandwidth, wavelength and/or using any protocol, including Wi-Fi, Bluetooth, a mesh-network, Z-wave, ZigBee or any other communications protocol and/or method. In addition, communications module 53 facilitates communication with any form of a wireless network 86 including a local network 88, a cellular network 90, a mesh network 92, a satellite network, and eventually the internet and/or the cloud. In one arrangement, communications module 53 includes a transceiver 54 and an antenna 56 among other components.

Transceiver:

Transceiver 54 is formed of any suitable size, shape and design and is configured to facilitate communication from and/or to tracking device 44. Transceiver 54 facilitates wireless communication in both reception as well as in transmission. In reception, transceiver 54 receives wireless signals from antenna 56 and filters and processes these signals and then transmits them to microprocessor 50 for further processing and interpretation according to instructions, software and/or code stored in memory 52. In transmission, transceiver 54 receives signals from microprocessor 50, which processes these signals and then transmits them over the air through antenna 56. While the term transceiver is conventionally used in association with an electronic device that facilitates reception as well as transmission of wireless signals, and it is contemplated that in most cases tracking device 44 will operate in both a reception mode as well as a transmitting mode, it is hereby to be understood that tracking device 44 may operate only in a transmission mode or only in a receiving mode, and the term transceiver as used herein is therefore intended to be interpreted to cover these modes of operation as well. When tracking device 44 operates only in a transmission mode, transceiver 54 operates as transmitter only and not a receiver. When tracking device 44 operates only in a reception mode, transceiver 54 operates as receiver only and not a transmitter.

Antenna 56 is formed of any suitable size, shape and design and is configured to receive wireless signals and/or transmit wireless signals. Antenna 56 is any interface between radio waves propagating through space and electric currents moving through conductors used in association with a receiver or transceiver. In transmission, antenna 56 radiates energy as electromagnetic waves (or radio waves). In reception, antenna 56 intercepts some of the power of an electromagnetic wave in order to produce an electric current which is amplified, processed and interpreted by transceiver 54 and/or microprocessor 50. Antenna 56 may be formed of any form of an antenna including a monopole antenna, a dipole antenna, a half-wave antenna, a broadband dipole antenna, a folded dipole antenna, a loop antenna, a cloverleaf antenna, a helical antenna, a spiral antenna, a corner reflector antenna, a parabolic reflector antenna, a rectangular microstrip antenna, a planar inverted-f antenna, a slot antenna, an inverted-f antenna, a NFC antenna, a Fractal antenna or any other form or configuration of an antenna. Antenna 56 facilitates the reception of information from the environment and/or antenna 56 facilitates the transmission of information to the environment, such as for purposes of communication with external components such as the wireless network 86, local network 88, cellular network 90, mesh network 92, internet 94 or the like.

Power source 58 is formed of any suitable size, shape and design and is configured to provide power to the electronic components of tracking device 44. In one arrangement, as one example, power source 58 is formed of one or more batteries that are contained within or as part of tracking device 44. The use of batteries as power source 58 allows for transportation of tracking device 44 and its attached medical device tray 34. The use of batteries as power source 58 however provides the disadvantage inherent with any limited power source; at some point in time the power source 58 will deplete. Another disadvantage to using batteries as power source 58 is that the functionality of batteries can be very weather dependent. As such, in extreme heat or cold the capacity of the batteries can be diminished thereby reducing the useful life of the batteries. As such, care is taken to ensure proper batteries are selected that have proper capacity and durability.

Controller 49 includes and/or is connected to any other physical and/or electronic component needed for operation. In one arrangement, controller 49 includes a keypad, one or more buttons and/or any other form of an entry device that facilitates user manipulation of tracking device 44 and/or entry of information such as a start, stop or unlock code or PIN code. In one arrangement, controller 49 includes a display that facilitates the display of information related to tracking device 44, such as battery life, ultimate destination (including address, planned arrival time and date, owner information, contents of the medical device tray 34, contact person information, and any other relevant needed or helpful information). In one arrangement, a touch screen device is used that facilitates the display of information as well as the entry of information and the manipulation of the tracking device 44.

Indicators:

In one arrangement, tracking device 44 includes an indicator 60. Indicator 60 is any device that indicates information about tracking device 44 to a person who sees or interacts with tracking device 44, such as whether the batteries are low, whether the tracking device 44 and its associated medical device tray 34 have gone lost or missing, whether the tracking device 44 and its associated medical device tray 34 are behind schedule, whether there is an error, or any other information. In one arrangement, indicator 60 is a visual indicator that provides a visual indication of information, such as a light that flashes and/or changes colors depending on the information that is to be portrayed. In another arrangement, indicator 60 is an audible indicator that provides an audible indication of information, such as a speaker. Indicator 60 may be any other form of a device that indicates information, and may include a display, as is described herein.

Sensors:

In one arrangement, tracking device 44 includes one or more sensors 62. Sensors 62 are formed of any suitable size, shape and design and is configured to sense states or environmental conditions applicable to tracking device 44. In one arrangement, sensors 62 include a motion sensor that detects when tracking device 44 is in motion. This may take the form of an accelerometer, a vibration sensor or any other sensor that detects movement or motion. In one arrangement, when sensor 62 detects movement or motion, signals from sensor 62 are used to change the state of tracking device 44 from an asleep-mode, wherein all or some of the electronic components of tracking device 44 are turned off or placed on reduced power consumption to conserve power, to an awake-mode, wherein all or some of the electronic components of tracking device 44 are turned on or placed on full power so as to facilitate functioning of the tracking device 44. Having the ability to go into an asleep-mode when the tracking device 44 is not moving has the potential to greatly extend the life of power source 58 as in many cases medical device tray 34 will remain idle and stationary for weeks or months at a time.

In another arrangement, sensor 62 may be any other form of a sensor, such as a temperature sensor, which tracks and logs the temperatures that medical device tray 34 is exposed to, an impact sensor, which tracks and logs the impacts that medical device tray 34 is exposed to, a location sensor, such as a GPS (Global Positioning System) sensor, that senses the position of the medical device tray 44, or any other form of a sensor that can be used to sense any other information or characteristic applicable to medical device tray 44.

Input:

In one arrangement, as one example, tracking device 44 includes an input 64. Input 64 is formed of any suitable size, shape and design and is configured facilitate connection of tracking device 44 to one or more external systems or components for any purpose such as recharging power source 58, updates, and for the purposes of communication, such as sending and/or receiving information in the form of electronic signals. In one arrangement, input 64 is formed of one or more dry contacts. In another arrangement, input 64 is a socket or plug, such as, for example, an RJ11 socket or plug (standard phone jack or plug), an RJ45 socket or plug (standard Ethernet jack or plug), a USB socket or plug, a micro-USB socket or plug, or any other form of a socket or plug. In another arrangement, input 64 is an induction coil that facilitates charging through inductance and in this arrangement antenna 56 is used to wirelessly connect to external systems or components for purposes of communication, such as through Wi-Fi, Bluetooth, a mesh-network, Z-wave, ZigBee or any other communications protocol and/or method.

Actuator:

In one arrangement, as one example, tracking device 44 includes an actuator 66. Actuator 66 is formed of any suitable size, shape and design and is configured facilitate actuation of tracking device 44. In one arrangement, actuator 66 is formed of a button or other input that can be used to actuate tracking device 44. In one arrangement, actuator 66 is used to turn tracking device 44 on or off. In another arrangement, actuator 66 is used to change tracking device 44 from an asleep state to an awake state, or from an awake state to an asleep state. Actuator 66 may be used for any other purpose.

Locking Device:

In one arrangement, as one example, tracking device 44 includes a locking device 68. Locking device 68 is formed of any suitable size, shape and design and is configured facilitate locking of tracking device 44 to medical device tray 34 and to prevent tampering with and/or removing tracking device 44 from medical device tray 34. The information provided by tracking device 44 does not have value unless tracking device 44 is and remains attached to medical device tray 34. The use and implementation of locking device 68 helps to insure that tracking device 44 remains associated with medical device tray 34.

In one arrangement, locking device 68 may be in the form of a conventional physical lock and key. In another arrangement, locking device 68 may be in the form of an electronic lock that is locked and/or unlocked through the entry of information, such as a code or PIN into input 64 or through a wireless transmission to tracking device 44. Locking device 68 may take on any other form of a locking device 68.

In one arrangement, locking device 68 is associated with a sensor 62. In this arrangement, when locking device 68 is unlocked, and the tracking device 44 is removed from medical device tray 44, tracking device 44 transmits a wireless signal informing users that the tracking device 44 has been locked and/or removed from medical device tray 34.

Third Party Intermediary:

In one arrangement, system 10 includes a third party intermediary 70. Third party intermediary 70 is any entity, service, company, person or other that provides tracking device 44 for use and facilitates tracking of tracking device 44 and medical device tray 34 during use. In one arrangement, third party intermediary 70 supplies tracking device 44 to distributor 24 to be associated with medical device tray 34.

In one arrangement, prior to distribution to distributor 24, third party intermediary 70 records information regarding tracking device 44 in its database 76, such as the unique ID or serial number of the tracking device 44 and any other information. When distributor 24 receives tracking device 44 distributor 24 associates itself with the tracking device 44 by establishing an account with third party intermediary 70 through user interface 72 by providing the unique ID or serial number of the tracking device and any other necessary information. Once distributor 24 has established an account, with third party intermediary 70, which is stored in database 76 distributor 24 is able to control operation of tracking device 44 within the parameters established by distributor 24.

Distributor 24 stores accounts for each tracking device 44. Also stored in database 76 is information 78 related to each tracking device 44 such as a log of locations 80 along with time and date information, events 82 along with time and date information, and contents 84, such as the types of medical devices 14 that are part of the attached medical device tray 34.

In one arrangement, when tracking device 44 is attached to medical device tray 34, and tracking device 44 is actuated, tracking device 44 intermittently and/or periodically senses its location and communicates with wireless network 86, such as a local network 88, a cellular network 90, and/or a mesh network 92 or any other network. When tracking device 44 is in wireless communication with wireless network 86, such as a local network 88, a cellular network 90, and/or a mesh network 92 or any other network tracking device 44 transmits information regarding itself to third party intermediary 70. That is, tracking device 44 transmits one or more signals over wireless network 86, such as a local network 88, a cellular network 90, and/or a mesh network 92 or any other network to third party intermediary 70. This information may contain the time, date and location of the tracking device 44, the status of the tracking device 44, the battery charge remaining of the tracking device 44 and any other information. Third party intermediary 70 stores the information contained in these signals or transmissions in database 76.

In one arrangement, users, such as distributor 24, sales rep 28, shipping agent 26, end user 30, patient 32 or any other person or entity that have been granted access to the information related to tracking device 44 may be transmitted periodic updates. That is, in one arrangement, third party intermediary 70 transmits a communication, such as a text message, email, voice mail or any other message, to users whenever an update is received from tracking device 44. In another arrangement, third party intermediary 70 transmits a communication, such as a text message, email, voice mail or any other message, to users on a predetermined periodic manner that provides an update regarding tracking device 44.

In one arrangement, users, such as distributor 24, sales rep 28, shipping agent 26, end user 30, patient 32 or any other person or entity, that have been granted access to the information related to tracking device 44 may check on the most recent status of tracking device 44 by connecting to third party intermediary 70, through wireless network 86, such as a local network 88, a cellular network 90, a mesh network 92 or any other network, and/or through the internet using a computing device, such as a computer, a laptop computer, a tablet, a smart phone or any other internet enabled device.

Upon connecting to third party intermediary 70 and database 76, the user may receive a real-time update regarding the location and status of tracking device 44. The user may also review the log of information 78 stored in database 76 including location 80, events 82 and contents 84, account information, settings information, and any other information. The user may also modify the operation of the tracking device 44, such as how often to connect and provide a status updates to third party intermediary 70 and the like. The user may also perform any other task allowed by third party intermediary 70.

In Operation:

In one arrangement, the medical device tray tracking system 10 presented herein operates in the following manner. Distributor 24 assembles a medical device tray 34, formed of an outer tray 36, a cover 38 and one or more inner trays 40, including medical devices 14, such as medical tools 16, medical implants 18, medical equipment 20 and medical consumables 22, from one or more medical device companies 12.

Distributor 24 receives a tracking device 44 from third party intermediary 70 and attaches the tracking device 44 to the medical device tray 34. In one arrangement, tracking device 44 is placed within the medical device tray 34. In another arrangement, tracking device 44 is attached to the exterior of the medical device tray 34. In another arrangement, tracking device 44 is attached to medical device tray 34 by any other manner, method or means.

Once assembled, and tracking device 44 is actuated, tracking device 44 senses the conditions around tracking device 44, such as whether tracking device 44 is in motion or at rest. In one arrangement, tracking device 44 toggles between an asleep-state, when tracking device is not moving, and an awake-state when tracking device 44 is moving. This provides substantial battery life savings as the medical device tray 34 is at rest most of the time. Tracking device 44 communicates through wireless network 86 to both determine the location of the tracking device 44 as well as transmit information to and/or from third party intermediary 70.

When third party intermediary 70 receives information from tracking device 44 through wireless network 86, third party intermediary 70 stores this information in database 76 in the form of a log of information 78 including location 80, events 82 and contents 84 of medical device tray 34. The information contained in database 76 and updates may be transmitted periodically to all users associated with the account associated with the tracking device 44, such as through a text message, a voice message, an email or by any other message. Event based updates may also be transmitted to the users, such as when the tracking device 44 senses it reached its final destination, when the tracking device 44 senses that it was detached from the medical device tray, when the tracking device 44 falls below a minimum power threshold, or any other event that is worthy of transmitting an event-based communication to the user.

In one arrangement, users may connect to third party intermediary 70 and request an immediate update of the status and location of tracking device 44. In this arrangement, third party intermediary 70, or another component of the system, transmits a signal to tracking device 44 and requests an update from the tracking device 44.

In this way, users are kept better informed regarding the status of the tracking device 44 and associated medical device tray 34 through periodic updates and/or event based updates.

From the above discussion it will be appreciated that the medical device tray tracking system and method of use presented herein improves upon the state of the art.

Specifically, the medical device tray tracking system and method of use presented herein: provides the ability to track the location of medical trays; improves the ability to track the location of medical trays; reduces lost or misplaced medical; reduces the cost of medical procedures; improves the efficiency of medical procedures; reduces the risk to medical sales reps for lost or misplaced medical trays; reduces insurance claims due to lost or misplaced medical trays; reduces the need to build or rebuild existing medical trays; improves the efficiency of our medical system; reduces the potential for delay in medical procedures due to a lost or misplaced medical tray; lowers the cost of healthcare; is easy to use; is safe to use; is easy to implement; is practically foolproof; does not substantially increase the cost of delivery; has a robust design; has a long, useful life; is durable; is relatively inexpensive; is high quality, among countless other advantages and improvements.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the disclosure. It is intended that this disclosure be limited only by the following claims and the full scope of equivalents thereof. All such modifications and changes of the disclosure fall within the scope of the claims and are intended to be covered thereby.

What is claimed:

1. A medical device tray tracking system, comprising:
    a medical device tray:
    the medical device tray having a plurality of medical devices thereon that are configured to be used in the performance of a medical procedure;
    a tracking device;
    the tracking device attached to the medical device tray;
    the tracking device having a housing;
    the tracking device having a controller having a microprocessor and memory;
    the tracking device having a communications module having a transceiver and an antenna that facilitates wireless communication;
    the tracking device having a power source that powers electronic components of the tracking device;
    a third party intermediary;
    the third party intermediary having a user interface and a database;
    wherein when the tracking device is attached to the medical device tray, the tracking device communicates through a wireless network over the internet and provides information regarding the tracking device and attached medical device tray to the third party intermediary;
    wherein when a user desires information regarding the tracking device and attached medical device tray, the user connects to the third party intermediary over an electronic network through the user interface; and
    wherein the tracking device includes a plurality of sensors configured and arranged to detect movement of the tracking device, track temperature the attached medical device tray is exposed to, and track impacts that the attached medical device tray is exposed to, and
detect whether the tracking device has been detached from the medical device tray.

2. The system of claim 1, wherein the information regarding the tracking device and attached medical device tray includes a present or most recent location.

3. The system of claim 1, wherein the information regarding the tracking device and attached medical device tray includes a log including the time and location of the tracking device and attached medical device tray.

4. The system of claim 1, wherein the tracking device periodically connects to the wireless network and provides the location of the tracking device and attached medical device tray to the third party intermediary.

5. The system of claim 1, wherein the plurality of sensors are further configured and arranged to detect whether the tracking device has been detached from the medical device tray.

6. The system of claim 1, wherein the tracking device includes a sensor, wherein the sensor detects whether the tracking device has been detached from the medical device tray.

7. The system of claim 1, wherein the third party intermediary periodically provides information regarding the location of the tracking device and attached medical device tray to the user through contact information.

8. The system of claim 1, wherein the wireless network is a local network.

9. The system of claim 1, wherein the wireless network is a cellular network.

10. The system of claim 1, wherein the wireless network is a mesh network.

11. The system of claim 1, wherein the plurality of medical devices include one of more of a set of medical devices including medical tools, medical implants, and medical equipment.

12. The system of claim 1, wherein the plurality of medical devices include medical implants.

13. The system of claim 1, wherein the plurality of medical devices include medical equipment.

14. The system of claim 1, wherein the intermediary device includes a database that stores a log of information regarding the tracking device and attached medical device tray.

15. A method of tracking medical device trays, the steps comprising:
providing a medical device tray, the medical device tray having a plurality of medical devices thereon that are configured to be used in the performance of a medical procedure:
providing a tracking device, the tracking device having a housing, the tracking device having a controller having a microprocessor and memory, the tracking device having a communications module having a transceiver and an antenna that facilitates wireless communication, the tracking device having a power source that powers electronic components of the tracking device;
attaching the tracking device to the medical device tray;
transporting the medical device tray;
periodically connecting to a wireless network by the tracking device;
providing location information of the medical device tray to a third party intermediary over the wireless network; and determining whether or not the tracker and the attached medical device tray are behind schedule based on the location information; and
using a visual indicator of the tracking device, providing an indication whether or not the tracker and the attached medical device tray are behind schedule.

16. The method of claim 15, further comprising the step of sending a message to a user regarding the location of the medical device tray.

17. The method of claim 15, further comprising the step of connecting to the intermediary device over the wireless network and thereby determining a location of the medical device tray by a user.

18. The method of claim 15, further comprising the step of storing a log including the time and location of the tracking device and attached medical device tray in a database by the third party intermediary.

19. The method of claim 15, wherein the tracking device includes a sensor, wherein the sensor detects movement of the tracking device.

20. The method of claim 15, wherein the tracking device includes a sensor, wherein the sensor detects whether the tracking device has been detached from the medical device tray.

21. The method of claim 15, wherein the wireless network is a local network.

22. The method of claim 15, wherein the wireless network is a cellular network.

23. The method of claim 15, wherein the wireless network is a mesh network.

24. The method of claim 15, wherein the plurality of medical devices include medical tools.

25. The method of claim 15, wherein the plurality of medical devices include medical implants.

26. The method of claim 15, wherein the plurality of medical devices include medical equipment.

27. The method of claim 15, wherein the tracking device transmits a signal to the third party intermediary in the event the tracking device is turned off.

28. The method of claim 15, wherein the tracking device transmits a signal to the third party intermediary in the event the tracking device is tampered with.

29. The method of claim 15, wherein the tracking device transmits a signal to the third party intermediary in the event the power source is depleted below a threshold.

30. The system of claim 5, wherein the tracking device includes a visual indicator configured and arranged to display status of the tracker and attached medical device tray based on data from the plurality of sensors.

31. The system of claim 30, wherein the visual indicator is configured and arranged to provide an indication whether or not the tracker and the attached medical device tray are behind schedule.

32. A tracker for tracking medical device trays, comprising:
a controller circuit having a microprocessor and memory;
a communications circuit having a transceiver and an antenna that facilitates wireless communication;
a power source that powers electronic components of the tracking device;
wherein the tracker intermittently connects to a wireless network and provides location information regarding the tracking device to an intermediary device; and
wherein the tracking device transmits a signal to the intermediary device in the event the tracking device is turned off.

33. A method of tracking medical device trays, the steps comprising:
- providing a medical device tray, the medical device tray configured to hold one or more medical devices thereon;
- attaching a tracking device to the medical device tray, the tracking device having a controller having a microprocessor and memory, the tracking device having a communications module having a transceiver and an antenna that facilitates wireless communication, the tracking device having a power source that powers electronic components of the tracking device;
- periodically connecting to a wireless network by the tracking device;
- providing location information of the tracking device to an intermediary device over the wireless network; and
- transmitting a signal to the intermediary device in the event the tracking device is turned off.

34. A medical device tray tracking system, comprising:
- a medical device tray:
- the medical device tray having a plurality of medical devices thereon that are configured to be used in the performance of a medical procedure;
- a tracking device;
- the tracking device attached to the medical device tray;
- the tracking device having a housing;
- the tracking device having a controller having a microprocessor and memory;
- the tracking device having a communications module having a transceiver and an antenna that facilitates wireless communication;
- the tracking device having a power source that powers electronic components of the tracking device;
- a third party intermediary;
- the third party intermediary having a user interface and a database;
- wherein when the tracking device is attached to the medical device tray, the tracking device communicates through a wireless network over the internet and provides information regarding the tracking device and attached medical device tray to the third party intermediary;
- wherein when a user desires information regarding the tracking device and attached medical device tray, the user connects to the third party intermediary over an electronic network through the user interface; and
- wherein the tracking device includes a plurality of sensors configured and arranged to track temperature the attached medical device tray is exposed to, and track impacts that the attached medical device tray is exposed to.

\* \* \* \* \*